US00PP22740P2

(12) United States Plant Patent
Zaiger et al.

(10) Patent No.: US PP22,740 P2
(45) Date of Patent: May 22, 2012

(54) INTERSPECIFIC TREE NAMED 'CRIMSON KAT'

(50) Latin Name: **Interspecific *prunus***
Varietal Denomination: Crimson Kat

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 4 days.

(21) Appl. No.: 12/927,684

(22) Filed: Nov. 22, 2010

(51) Int. Cl.
*A01H 5/00* (2006.01)

(52) U.S. Cl. ..... Plt./180

(58) Field of Classification Search ..... Plt./180
See application file for complete search history.

(56) References Cited

U.S. PATENT DOCUMENTS

PP11,630 P * 11/2000 Zaiger et al. ..... Plt./197

OTHER PUBLICATIONS

UPOV-ROM Pluto, Plant Variety Database, 2011-04 GTI Jouve Retrival Software, citation for 'Sweet Blaze' (2 pages total).*

* cited by examiner

*Primary Examiner* — Susan McCormick Ewoldt

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit with attractive red flesh color.
2. Fruit with very good flavor and eating quality.
3. Fruit with a good balance between sugar and acid with an average Brix of 19.6°.
4. Fruit with good storage and shipping quality.
5. The tree with vigorous upright growth habit.

1 Drawing Sheet

Botanical classification: Interspecific *Prunus* species

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plums, apricots and interspecific trees, which are known to us, and mentioned herein, 'Mariposa' Plum (U.S. Plant Pat. No. 111), 'Red Beaut' Plum (U.S. Plant Pat. No. 2539), 'Flaming Gold' Apricot (U.S. Plant Pat. No. 2822) and 'Flavor Treat' Interspecific (U.S. Plant Pat. No. 12,936).

STATEMENT REGARDING FEDERALLY SPONSORED RESEARCH AND DEVELOPMENT

Not applicable.

ORIGIN OF THE VARIETY

The new and distinct interspecific tree consists of the combination of *Prunus salicina, Prunus armeniaca* and *Prunus*

*persica*. It was originated by us in our experimental orchard located near Modesto, Calif. as a first generation cross between two proprietary lines of interspecific trees with field identification numbers '82EG355' and '295LF401'. The seed parent (82EG355) originated from a cross between the following, 'Mariposa' Plum (U.S. Plant Pat. No. 111), proprietary plumcots '4G1180', '42GA580' and '4G720' and a proprietary peachcot '10W100' seedling that originated from a cross of 'Flaming Gold' Apricot (U.S. Plant Pat. No. 2822) with a peach of unknown parentage. All of the plumcots are seedlings of 'Red Beaut' Plum (U.S. Plant Pat. No. 2539) crossed with an apricot of unknown parentage. The pollen parent (295LF401) originated from crosses of the following parents 'Mariposa' Plum (U.S. Plant Pat. No. 111), proprietary plumcots '4G1180', '4G720', '42GA580' and the peachcot '10W100' that is a seedling of 'Flaming Gold' Apricot (U.S. Plant Pat. No. 2822) crossed with a peach of unknown parentage. A large number of these first generation crosses were planted and grown on their own root system. Under close and careful observations, one such seedling exhibited desirable fruit characteristics and was selected in 2000 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and show that reproductions run true to the original tree and all characteristics of the tree and its fruit are established and transmitted through succeeding asexual propagations.

SUMMARY OF THE NEW VARIETY

A new and distinct variety of interspecific tree [(Plum×Plumcot)×(Plumcot)×(Plum×Plumcot)×(Peach Cot)]×[(Plum×Plumcot)×(Plumcot)×(Plum×Plumcot)×(Peach Cot)], which is of medium to large in size, vigorous, upright growth and a regular and productive bearer of medium to large, red flesh fruit with very good flavor and eating quality. The fruit is further characterized by its firm flesh, its good storage and shipping quality and having a good balance between acid and sugar. In comparison to its seed parent (82EG355) the fruit of the new variety has dark red flesh instead of yellow-red flesh and is approximately 10 days later in maturity. In comparison to its pollen parent (295LF401) the fruit of the new variety has smooth skin instead of pubescent, has dark red flesh instead of yellow and is approximately 90 days later in maturity. In comparison to the late ripening interspecific 'Flavor Treat' (U.S. Plant Pat. No. 12,936) the fruit of the new variety has red flesh instead of yellow and matures approximately 4 days later.

PHOTOGRAPH OF THE VARIETY

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, 9 years of age, its flowers, foliage and fruit, as based on observations of 9 year old specimens grown near Modesto, Calif., with color in accordance with Munsell Book of Color.

Tree:

*Size*.—Large, pruned to 3 to 3.5 meters in height and width for economical harvesting of fruit.

*Vigor*.—Vigorous. Growth of 1.5 to 2 meters the first growing season, varies with type of soil, fertility and cultural practices.

*Form*.—Upright, similar to standard plum trees.

*Branching Habit*.—Upright, crotch angle approximately 35°, increases with heavy production.

*Productivity*.—Productive. Sets 1.5 to several times the amount of fruit desired, thinning and spacing of fruit necessary for marketable size fruit. Varies with climatic conditions during bloom time.

*Bearer*.—Regular. Good fruit set for 7 consecutive years. No alternate bearing observed.

*Fertility*.—Self-sterile, pollinator required.

*Density*.—Medium dense. Usually pruned to vase shape to increase amount of sunlight to center of tree to enhance fruit color, Brix and health of fruit wood.

*Hardiness*.—Tree grown in USDA Hardiness Zone 9. Winter chilling requirement is approximately 600 hours at or below 45° F. Hardy in all stone fruit growing areas of California.

Trunk:

*Size*.—Large. Average circumference of 91.4 cm at 25.4 cm above ground on a 9 year old tree.

*Stocky*.—Medium stocky.

*Texture*.—Medium shaggy, increases with age of tree.

*Color*.—Varies from 7.5YR 3/2 to 10YR 2/2.

Branches:

*Size*.—Medium. Average circumference of 14.9 cm when measured at a height of 1.3 meters above ground. Crotch angle approximately 35°, increases with heavy crop load.

*Surface texture*.—New growth relatively smooth. Mature growth moderately rough, roughness increases with age.

*Lenticels*.—Average number 27 in a 25.8 sq cm section. Average length 3.3 mm. Average width 1.1 mm. Color varies from 5YR 5/8 to 7.5YR 5/8.

*Color*.—New growth varies from 5GY 6/6 to 5GY 5/6. Mature growth varies from 5Y 3/2 to 5Y 2/2, varies with age of growth.

Leaves:

*Size*.—Large. Average length 110.7 mm. Average width 46.0 mm.

*Form*.—Oblanceolate.

*Apex*.—Acuminate.

*Base*.—Cuneate.

*Margin*.—Serrate.

*Thickness*.—Medium.

*Surface texture*.—Upper surface relatively smooth, slight indentation over midrib and leaf veins, glabrous. Lower surface relatively smooth, except for small ridges created by midrib and pinnate venation, glabrous.

*Petiole*.—Small to medium. Average length 11.4 mm. Average width 1.7 mm. Grooved longitudinally. Surface glabrous. Color varies from 2.5GY 6/6 to 2.5GY 5/6.

*Glands*.—Globose. Number varies from 1 to 3, average number 2. Size — small. Average length 0.4 mm. Average width 0.2 mm. Located on the base of the leaf blade and upper portion of the petiole. Color varies from 2.5Y 4/4 to 2.5Y 5/4.

*Color*.—Upper surface varies from 7.5GY 3/2 to 7.5GY 2/4. Lower surface varies from 7.5GY 5/4 to 7.5GY 4/2. Midvein color varies from 2.5GY 7/4 to 2.5GY 6/4.

Flower buds:

*Size*.—Small to medium. Average length 8.5 mm. Average diameter 4.3 mm.

*Hardiness*.—Hardy with respect to California winters.

*Form*.—Plump, conical, becomes more elongated as bud matures.

*Pedicel*.—Average length 10.9 mm. Average width 0.4 mm. Color varies from 2.GY 6/6 to 2.5GY 6/8.

*Color*.—N 9.5/(white).

*Number of buds per spur*.—Varies from 10 to 13, average number 12.

Flowers:

*Size*.—Small to medium. Average height 10.6 mm. Average diameter 18.9 mm.

*Petals*.—Number 5, alternately arranged to sepals. Size — medium. Average length 10.6 mm. Average width 6.7 mm. Form — elliptical. Margin — entire. Both upper and lower surfaces glabrous. Color N 9.5/(white).

*Sepals*.—Number 5, alternately arranged to petals. Size — small. Average length 2.8 mm. Average width 2.3 mm. Shape — triangular. Margin — entire. Both upper and lower surfaces glabrous. Color — upper surface varies from 2.5GY 6/6 to 5GY 7/6. Lower surface varies from 2.5GY 6/8 to 5GY 7/6.

*Stamens*.—Average number per flower 30. Average filament length 7.4 mm. Filament color N 9.5/(white). Anther color varies from 5Y 8.5/10 to 5Y 8/10.

*Pollen*.—Present, self sterile, pollinator required. Color varies from 5Y 8/8 to 5Y 7/10.

*Pistil*.—Normally 1. Average length 9.3 mm. Position of stigma — average 1.2 mm below anthers. Color varies from 10Y 8.5/4 to 2.5GY 8/6. Surface — glabrous.

*Fragrance*.—Strong fragrance.

*Blooming period*.—Date of First Bloom Feb. 20, 2010. Date of Petal Fall Feb. 28, 2010, varies slightly with climatic conditions.

*Color*.—N 9.5/(white).

*Number flowers per flower bud*.—Average 3, varies from 1 to 3.

*Pedicel*.—Average length 12.1 mm. Average width 0.4 mm. Color varies from 2.5GY 6/8 to 5GY 7/10. Surface — glabrous.

Fruit:

*Maturity when described*.—Firm ripe.

*Date of first picking*.—Sep. 10, 2010.

*Date of last picking*.—Sep. 18, 2010, varies slightly with climatic conditions.

*Size*.—Medium to large. Average diameter axially 62.7 mm. Average transversely in suture plane 65.1 mm. Average weight 153.4 grams, varies slightly with fertility of the soil, amount of thinning and climatic conditions.

*Form*.—Globose.

*Suture*.—Nearly smooth, extends from base to apex.

*Ventral surface*.—Nearly smooth.

*Apex*.—Varies from rounded to slight tip.

*Base*.—Varies from flat to slightly retuse.

*Stem cavity*.—Rounded to slightly elongated in suture plane. Average depth 8.7 mm. Average diameter 8.5 mm.

Stem:

*Size*.—Medium to large. Average length 20.9 mm. Average diameter 1.5 mm.

*Color*.—Varies from 2.5YR 3/4 to 5YR 3/6.

Flesh:

*Ripens*.—Evenly.

*Texture*.—Firm.

*Fibers*.—Few, small, tender.

*Firmness*.—Firm, having good handling and shipping quality.

*Aroma*.—Slight.

*Amydgalin*.—Undetected.

*Eating quality*.—Very good.

*Flavor*.—Very good, good balance between acid and sugar.

*Juice*.—Moderate amount, enhances flavor.

*Brix*.—Average Brix 19.6°, varies slightly with amount of fruit per tree and climatic conditions.

*Color*.—Varies between 5R 4/12 to 5R 3/10. Pit cavity varies between 5R 2/4 to 5R 3/10.

Skin:

*Thickness*.—Medium.

*Surface*.—Smooth to slightly waffled.

*Bloom*.—Moderate amount.

*Tendency to crack*.—Very slight.

*Color*.—Ground color varies from 7.5Y 8.5/4 to 10Y 8.5/4. Overspread with 5R 3/6 to 5R 2/4. Some fruit with small, randomly spaced areas of ground color exposed to give a slight speckling pattern to some skin surface areas.

*Tenacity*.—Tenacious to flesh.

*Astringency*.—Undetected.

Stone:

*Type*.—Clingstone.

*Size*.—Medium. Average length 26.8 mm. Average width 19.2 mm. Average thickness 11.1 mm.

*Form*.—Ovoid.

*Base*.—Usually flat, varies from flat to rounded.

*Apex*.—Acuminate. Average length 2.7 mm.

*Surface*.—Very lightly pitted throughout. One shallow groove on each side of suture extending from base to apex. Very small, short ridges running from base towards apex approximately ¼ distance of stone.

*Sides*.—Unequal, one side extending further outward from suture plane.

*Ridges*.—Very small and short extending from base toward apex on some stones.

*Tendency to split*.—None.

*Color*.—Varies from 5YR 4/6 to 7.5YR 4/6 when dry.

Kernel:

*Form*.—Ovate.

*Taste*.—Bitter.

*Viability*.—Viable, complete embryo development.

*Size*.—Medium. Average length 14.1 mm. Average width 10.0 mm. Average depth 5.7 mm.

*Skin*.—Color varies from 2.5Y 8/6 to 10YR 6/6.

Use: Dessert.

*Market*.—Local and long distance.

Keeping quality: Good, held firm in cold storage (38-42° F.) for 3 weeks without internal breakdown of flesh or appreciable loss of flavor.

Shipping quality: Good, showed minimal skin scarring or flesh bruising of fruit in picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

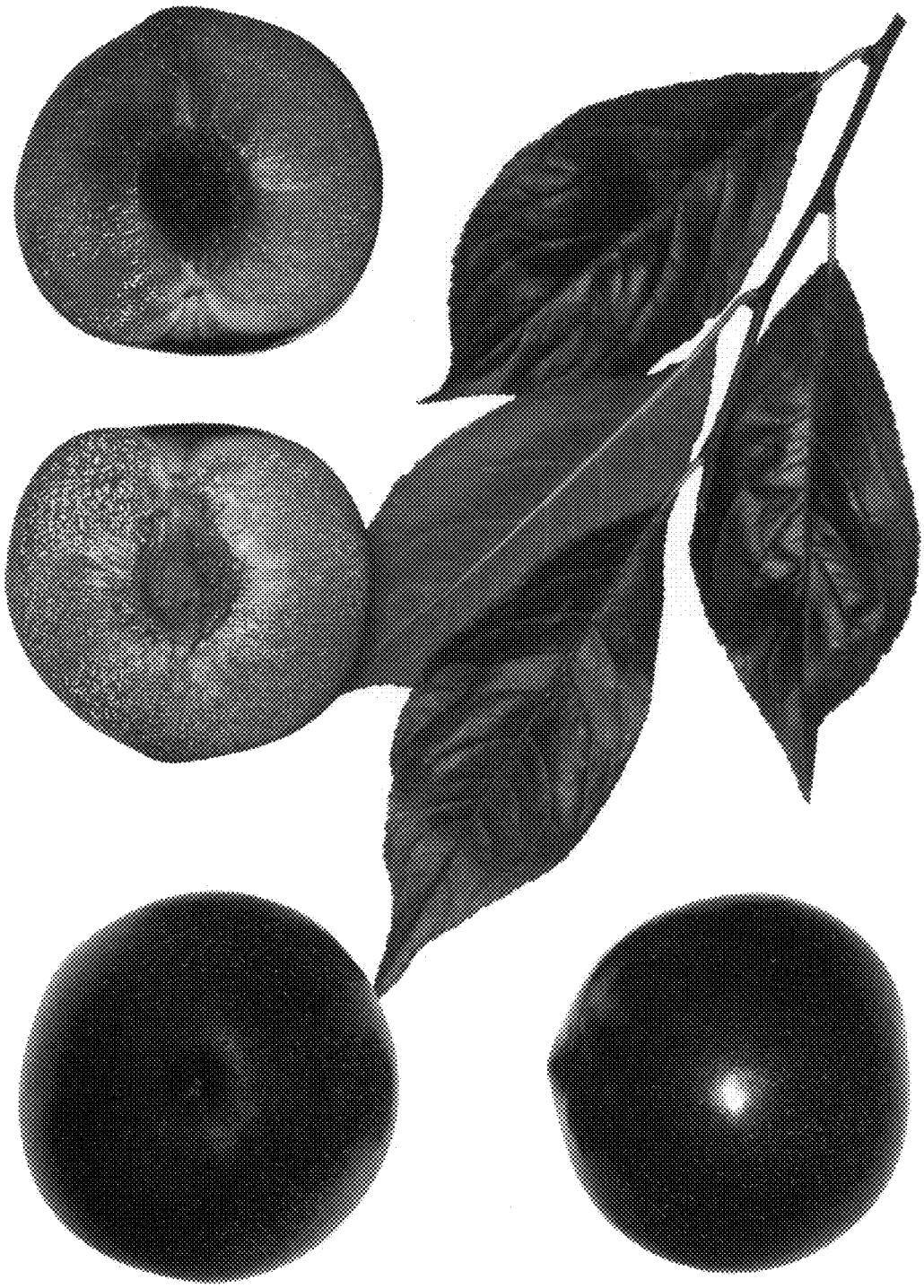

* * * * *